(12) United States Patent
Dave et al.

(10) Patent No.: US 6,998,485 B1
(45) Date of Patent: Feb. 14, 2006

(54) POLYAZIDO COMPOUNDS

(75) Inventors: Paritosh R. Dave, Bridgewater, NJ (US); Raja G. Duddu, Parsipanny, NJ (US); Reddy Damavarapu, Hackettstown, NJ (US); Nathaniel Gelber, Randolph, NJ (US); Kathy Yang, Flanders, NJ (US); C. Rao Surapaneni, Long Valley, NJ (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 358 days.

(21) Appl. No.: 10/604,775

(22) Filed: Aug. 15, 2003

Related U.S. Application Data

(60) Provisional application No. 60/319,801, filed on Dec. 19, 2002.

(51) Int. Cl.
| | |
|---|---|
| *C07D 471/00* | (2006.01) |
| *C07D 487/00* | (2006.01) |
| *C07D 491/00* | (2006.01) |
| *C07D 495/00* | (2006.01) |
| *C07D 497/00* | (2006.01) |

(52) U.S. Cl. .................................................. 544/346

(58) Field of Classification Search ................. 544/346
See application file for complete search history.

*Primary Examiner*—James O. Wilson
*Assistant Examiner*—Zachary C. Tucker
(74) *Attorney, Agent, or Firm*—Robert Charles Beam; John F. Moran

(57) ABSTRACT

The compound 3a,8a-bis-azidomethyl-3a,4,8a,9-tetrahydro-3H,8H-bis-[1,2,3]triazolo[1,5-a;1",5"-d]pyrazine, whose structure is depicted below, is disclosed:

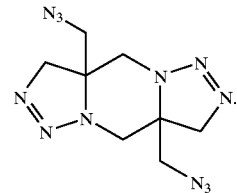

1 Claim, No Drawings

POLYAZIDO COMPOUNDS

CROSS REFERENCE TO RELATED APPLICATIONS

This application claims benefit under 35 USC 119(e) of provisional application 60/319,801, filed Dec. 19, 2002, the entire file wrapper contents of which provisional application are herein incorporated by reference as though fully set forth at length.

FEDERAL RESEARCH STATEMENT

This invention described herein may be made, used, or licensed by or for the United States Government for Government purposes without the payment of any royalties thereon or therefore.

BACKGROUND OF INVENTION

1. Field of the Invention

The present invention relates to novel polyazido compounds of the general formulae:

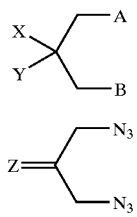

1. X=$N_3$; Y=$CH_2N_3$; A=B=$N_3$
2. X=OH; Y=$CH_2N_3$; A=B=$N_3$
3. X=$ONO_2$; Y=$CH_2N_3$; A=B=$N_3$
4. X=$NO_2$ Y=$CH_2N_3$; A=B=$N_3$
5. X=Y=$NO_2$; A=B=$N_3$
12. X=Y=$NO_2$; A=B=

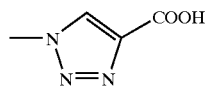

13. X=OH; A=B=

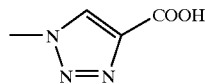

Y=

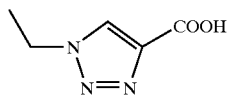

6. Z=$CH_2$
7. Z=O
8. Z=NOH

7-DNPH. Z=

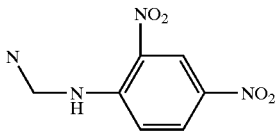

including 2-azido-2-azidomethyl-1,3-diazidopropane (1), 2-azidomethyl-2-hydroxy-1,3-diazidopropane (2), 2-azidomethyl-2-nitrato-1,3-diazidopropane (3), 2-azidomethyl-2-nitro-1,3-diazidopropane (4), 2,2-dinitro-1,3-diazidopropane (5), methallyldiazide (6), a dimer of methallyldiazide (6), comprising 3a,8a-Bis-azidomethyl-3a,4,8a,9-tetrahydro-3H,8H-bis[1,2,3]triazolo[1,5-a; 1", 5"-d]pyrazine (6-Dimer), 1,3-diazidoacetone (7), and 2-Oximido-1,3-diazidopropane (8).

Also shown are reaction intermediates of these compounds, including 2,2-bis(chloromethyl)oxirane (9), and 2,2-bis(azidomethyl)oxirane (10).

In addition, a number of potentially useful energetic compounds have been prepared from the low molecular weight polyazido compounds above, including N-2(azido-1-azidomethyl-ethylidene)-N"-(2,4-dinitrophenyl)-hydrazine (7-DNPH), 1,3-Bis(4-carboxytriazolyl)2,2-dinitropropane (12), Tris(4-carboxytriazolomethyl)methanol (13), Benzene-1,3,5-tricarboxylic acid tris(2-azido-1,1-bisazidomethyl-ethyl)ester (14), Adamantane 1,3,5,7-tetracarboxylic acid tetrakis(2-azido-1,1-bisazidomethyl-ethyl)ester (15), Adamantane carboxylic acid 2-azido-1,1-bisazidomethyl-ethyl)ester (16), cubane 1,3,5,7-tetracarboxylic acid tetrakis (2-azido-1,1-bisazidomethyl-ethyl)ester (17), cubane 1,4-dicarboxylic acid bis(2-azido-1,1-bisazidomethyl-ethyl)ester (18).

In particular, the present invention relates to 3a,8a-Bisazidomethyl-3a,4,8a,9-tetrahydro-3H,8H-bis[1,2,3]triazolo [1,5-a; 1",5"-d]pyrazine (6-Dimer).

2. Description of Related Art

Low molecular weight compounds substituted with multiple energetic groups exemplified by azide, nitrato and nitro groups are of interest as energetic plasticizer ingredients, monopropellant formulations and as building blocks for energetic polymers. Pentaerythritol tetranitrate, PETN, is widely used in blasting caps and detonation cords, bis (dinitropropyl)acetal/formal, BDNPA/F, azidomethyl-methyloxetane (AMMO) and bis(azidomethyl)oxetane (BAMMO) are commonly used plasticizer ingredients. Azido derivatives of pentaerythritol have been previously described (Frankel et al. U.S. Pat. No. 4,683,086). It was of interest to prepare compounds based on three- and four-carbon units with up to four energetic groups thus producing compounds with a higher proportion of energetic groups per mole than the pentaerythritol derivatives. The structural unit of one of the compounds presented herein, 2-azidomethyl-2-hydroxy-1,3-diazidopropane (compound 2, vide infra), has been incorporated into energetic plasticizers formals and acetals (Rindone et al. U.S. Pat. No. 5,220,039) but the subject alcohol 2-azidomethyl-2hydroxy-1,3-diazidopropane 2 has not previously been prepared.

CAUTION: All organic azides described herein should be considered extremely sensitive explosive compounds and should only be handled with proper safety precautions. 1,3-Diazidoacetone exploded subsequent to purification by distillation and extreme caution is urged in dealing with all the azides.

These compounds are expected to be useful in novel explosive and propellant applications as well as to serve as building blocks for the preparation of novel energetic polymers capitalizing on the high reactivity of the azido groups. As a comparison PETN has four energetic groups on a five-carbon framework whereas some of the compounds described herein have four energetic groups on a four- and a three-carbon unit. They are thus expected to provide much higher energy upon decomposition. The azido groups in these molecules can be converted to triazole and tetrazole to prepare high nitrogen materials of interest in gas generating applications. The ability of azido groups to undergo 1,3-dipolar cycloadditions, make these polyazido compounds useful starting materials for polymeric materials synthesis. In addition, the polyazidopolyesters derived form polycarboxylic acids and the alcohol 2-azidomethyl-2-hydroxy-1,3-diazidopropane 2, are of interest as core molecules for the synthesis of dendrimers.

This invention relates to a series of novel compounds having the general structures A and B:

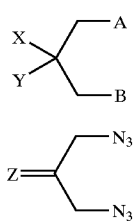

1. X=N$_3$; Y=CH$_2$N$_3$; A B=N$_3$
2. X=OH; Y=CH$_2$N$_3$; A=B=N$_3$
3. X=ONO$_2$; Y=CH$_2$N$_3$; A=B N$_3$
4. X=NO$_2$ Y=CH$_2$N$_3$; A=B=N$_3$
5. X=Y=NO$_2$; A=B=N$_3$
12. X=Y=NO$_2$; A=B=

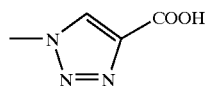

13. X=OH; A=B=

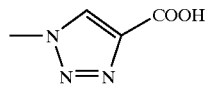

Y=

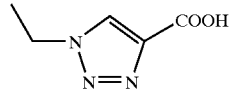

6. Z=CH$_2$
7. Z=O
8. Z=NOH

7-DNPH. Z=

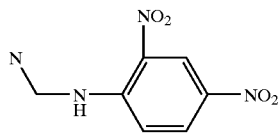

including 2-azido-2-azidomethyl-1,3-diazidopropane (1), 2-azidomethyl-2-hydroxy-1,3-diazidopropane (2), 2-azidomethyl-2-nitrato-1,3-diazidopropane (3), 2-azidomethyl-2-nitro-1,3-diazidopropane (4), 2,2-dinitro-1,3-diazidopropane (5), methallyldiazide (6), a dimer of methallyldiazide (6), comprising 3a,8a-Bis-azidomethyl-3a,4,8a,9-tetrahydro-3H,8H-bis[1,2,3]triazolo[1,5-a; 1", 5"-d]pyrazine (6-Dimer), 1,3-diazidoacetone (7), and 2-Oximido-1,3-diazidopropane (8).

Also shown are reaction intermediates of these compounds, including 2,2-bis(chloromethyl)oxirane (9), and 2,2-bis(azidomethyl)oxirane (10).

In addition, a number of potentially useful energetic compounds have been prepared from the low molecular weight polyazido compounds above, including N-2(azido-1-azidomethyl-ethylidene)-N"-(2,4-dinitrophenyl)-hydrazine (7-DNPH), 1,3-Bis(4-carboxytriazolyl)2,2-dinitropropane (12), Tris(4-carboxytriazolomethyl)methanol (13), Benzene-1,3,5-tricarboxylic acid tris(2-azido-1,1-bisazidomethyl-ethyl)ester (14), Adamantane 1,3,5,7-tetracarboxylic acid tetrakis(2-azido-1,1-bisazidomethyl-ethyl)ester (15), Adamantane carboxylic acid 2-azido-1,1-bisazidomethyl-ethyl)ester (16), cubane 1,3,5,7-tetracarboxylic acid tetrakis (2-azido-1,1-bisazidomethyl-ethyl)ester (17), cubane 1,4-dicarboxylic acid bis(2-azido-1,1-bisazidomethyl-ethyl)ester (18).

3. Objects of the Invention

It is an object of the present invention to provide low molecular weight energetic compounds with multiple energetic groups.

The other objects, features and advantages of the present invention will become more apparent in light of the following detailed description of the preferred embodiment thereof.

SUMMARY OF INVENTION

According to the present invention, there are provided low molecular weight polyazido compounds of the general formulae:

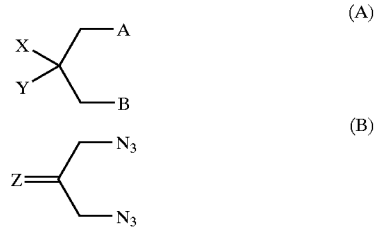

1. X=N$_3$; Y=CH$_2$N$_3$; A=B=N$_3$
2. X=OH; Y=CH$_2$N$_3$; A=B=N$_3$
3. X=ONO$_2$; Y=CH$_2$N$_3$; A=B=N$_3$
4. X=NO$_2$Y=CH$_2$N$_3$; A=B=N$_3$
5. X=Y=NO$_2$; A=B=N$_3$
12. X=Y=NO$_2$; A=B=

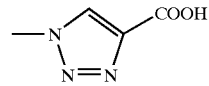

13. X=OH; A=B=

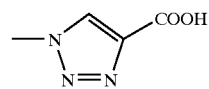

Y=

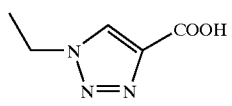

6. Z=CH$_2$
7. Z=O
8. Z=NOH

7-DNPH. Z=

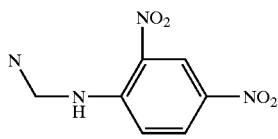

including 2-azido-2-azidomethyl-1,3-diazidopropane (1), 2-azidomethyl-2-hydroxy-1,3-diazidopropane (2), 2-azidomethyl-2-nitrato-1,3-diazidopropane (3), 2-azidomethyl-2-nitro-1,3-diazidopropane (4), 2,2-dinitro-1,3-diazidopropane (5), methallyldiazide (6), a dimer of methallyldiazide (6), comprising 3a,8a-Bis-azidomethyl-3a,4,8a,9-tetrahydro-3H,8H-bis[1,2,3]triazolo[1,5-a; 1", 5"-d]pyrazine (6-Dimer), 1,3-diazidoacetone (7), and 2-Oximido-1,3-diazidopropane (8).

Also shown are reaction intermediates of these compounds, including 2,2-bis(chloromethyl)oxirane (9), and 2,2-bis(azidomethyl)oxirane (10).

In addition, a number of potentially useful energetic compounds have been prepared from the low molecular weight polyazido compounds above, including N-2(azido-1-azidomethyl-ethylidene)-N"-(2,4-dinitrophenyl)-hydrazine (7-DNPH), 1,3-Bis(4-carboxytriazolyl)2,2-dinitropropane (12), Tris(4-carboxytriazolomethyl)methanol (13), Benzene-1,3,5-tricarboxylic acid tris(2-azido-1,1-bisazidomethyl-ethyl)ester (14), Adamantane 1,3,5,7-tetracarboxylic acid tetrakis(2-azido-1,1-bisazidomethyl-ethyl)ester (15), Adamantane carboxylic acid 2-azido-1,1-bisazidomethyl-ethyl)ester (16), cubane 1,3,5,7-tetracarboxylic acid tetrakis (2-azido-1,1-bisazidomethyl-ethyl)ester (17), cubane 1,4-dicarboxylic acid bis(2-azido-1,1-bisazidomethyl-ethyl)ester (18).

In particular, the present invention provides 3a,8a-Bis-azidomethyl-3a,4,8a,9-tetrahydro-3H,8H-bis[1,2,3]triazolo[1,5-a; 1", 5"-d]pyrazine (6-Dimer).

DETAILED DESCRIPTION

The preparation of the compounds claimed herein is detailed below.

The compounds 2-azido-2-azidomethyl-1,3-diazidopropane 1, 2-azidomethyl-2-hydroxy-1,3-diazidopropane 2, and 2-azidomethyl-2-nitrato-1,3-diazidopropane 3 were prepared as shown in Scheme 1.

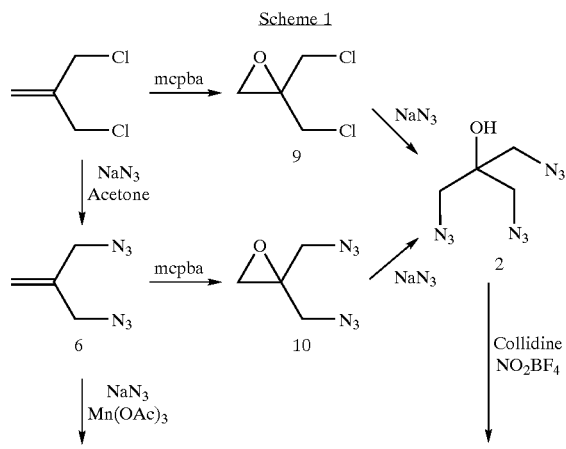

Commercially available methallyl dichloride was treated with sodium azide in acetone under reflux for 16 hours to obtain methallyldiazide, 6. Treatment of methallyldiazide 6 with sodium azide and manganese (III) acetate in acetic acid (J. Org. Chem. 1985, 50, 3647) afforded 2-azido-2-azidomethyl-1,3-diazidopropane 1 as a clear colorless liquid.

The preparation of 2-azidomethyl-2-hydroxy-1,3-diazidopropane 2 was achieved by two different routes. In one method, methallyl diazide was converted to the corresponding epoxide, 2,2-bis(azidomethyl)oxirane 10, by treatment with m-chloroperoxybenzoic acid (mcpba) in refluxing dichloroethane, which upon treatment with sodium azide provided 2-azidomethyl-2-hydroxy-1,3-diazidopropane 2. In a second method methallyl dichloride was converted to 2,2-bis(chloromethyl)oxirane 9 as described by Treves et al. (Chem. and Ind. 1971, 544). Treatment of 2,2-bis(chloromethyl)oxirane 9 with sodium azide led to the formation of 2-azidomethyl-2-hydroxy-1,3-diazidopropane 2.

2-Azidomethyl-2-hydroxy-1,3-diazidopropane 2 was converted to the corresponding nitrate, 2-azidomethyl-2-nitrato-1,3-diazidopropane 3, by treatment with nitronium tetrafluoroborate in the presence of collidine.

The preparation of 2-azidomethyl-2-nitro-1,3-diazidopropane 4, is depicted in Scheme 2.

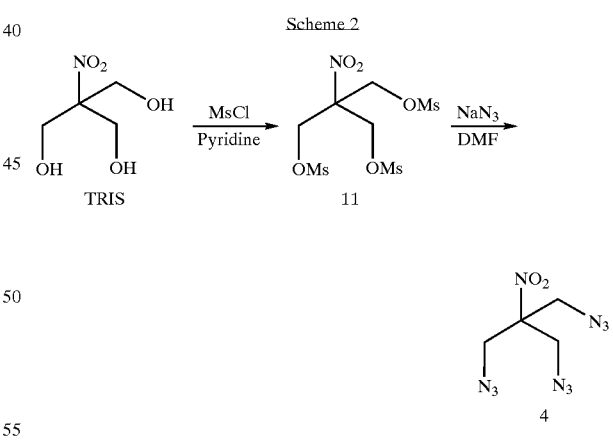

Commercially available tris(hydroxymethyl)nitromethane, (TRIS), was converted to the corresponding trimesylate, methanesulfonic acid 3-methanesulfonyloxy-2-methanesulfonyloxymethyl-2-nitro-propyl ester 11 according to a literature procedure (Wuest et al. Synthesis 1987, 742). Treatment of 3-methanesulfonyloxy-2-methanesulfonyloxymethyl-2-nitro-propyl ester 11 with sodium azide in dimethylformamide at elevated temperature afforded 2-azidomethyl-2-nitro-1,3-diazidopropane 4. The preparation of 1,3-diazido-2,2-dinitropropane 5 is shown in Scheme 3.

Scheme 3

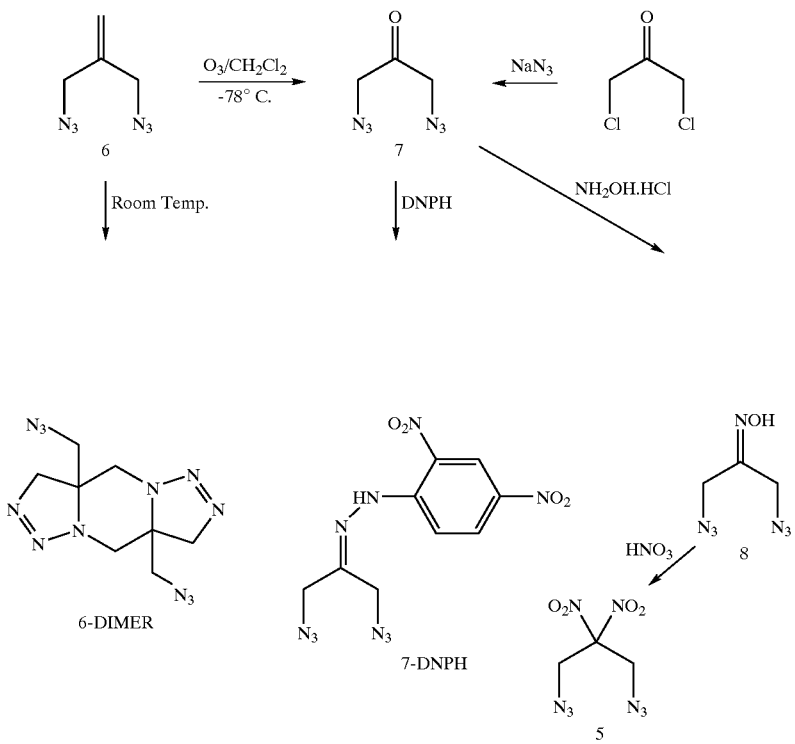

Ozonation of methallyldiazide, 6, in methylene chloride provided 1,3-diazidoacetone, 7, which was converted to its dinitrophenylhydrazone derivative, 7-DNPH. 1,3-diazidoacetone 7 was also prepared in one step from 1,3-dichloroacetone by reaction with sodium azide. The structure of 7-DNPH was established unequivocally by x-ray crystallographic analysis.

1,3-Diazidoacetone 7 was further converted to the corresponding oxime, 2-oximido-1,3-diazidopropane 8, which was subjected to nitration to obtain 2,2-dinitro-1,3-diazidopropane, 5. A further tricyclic compound, 3a,8a-bis-azidomethyl-3a,4,8a,9-tetrahydro-3H,8H-bis[ 1,2,3]triazolo[1, 5-a; 1", 5"]pyrazine 6-DIMER was obtained from a slow dimerization of methallyl diazide at room temperature over several days.

The 1,3-dipolar cycloaddition reaction of organic azides with various dienophiles with electron withdrawing groups is well established. The polyazides described herein can be treated with such dienophiles to synthesize novel heterocyclic molecules.

To demonstrate the ease of such reactions, the polyazido compounds 2,2-dinitro-1,3-diazidopropane 5 and 2-azidomethyl-2-hydroxy-1,3-diazidopropane 2 were treated with commercially available propiolic acid under thermal conditions to obtain the corresponding triazoles, 1,3-bis(4-carboxytriazolyl)-2,2-dinitropropane 12 and tris(4-carboxytriazolomethyl)methanol 13 respectively (Scheme 4).

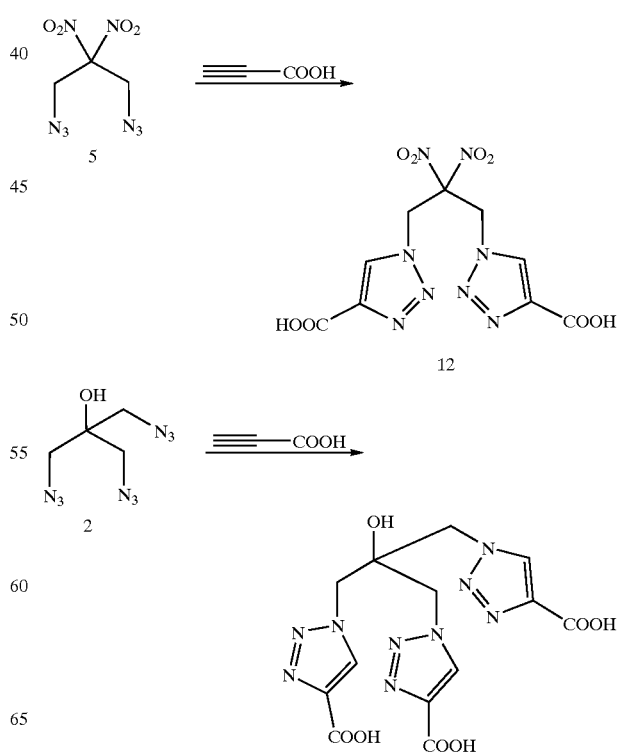

The diazido compounds prepared herein are expected to be important intermediates in the preparation of energetic polymers due to their high reactivity with acetylenic and other unsaturated compounds. The facile reaction of the azido group with dipolarophiles as exemplified by the preparation of the triazoles, 1,3-bis(4-carboxytriazolyl)-2,2-dinitropropane 12 and tris(4-carboxytriazolomethyl)methanol 13, can be exploited to provide polymeric materials by reaction with molecules containing multiple acetylenic functions or other unsaturated units as depicted in Scheme 5.

Scheme 5

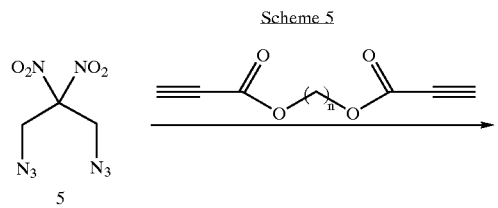

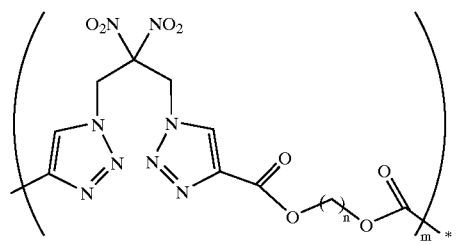

Another area of important utility of polyfunctionalized units is in the synthesis of dendrimers. The triazdioalcohol 2-azidomethyl-2-hydroxy-1,3-diazidopropane 2 was treated with a variety of poycarboxylic acid chlorides with rigid structures to obtain the corresponding polyazidopolyesters shown below (Scheme 6).

Scheme 6

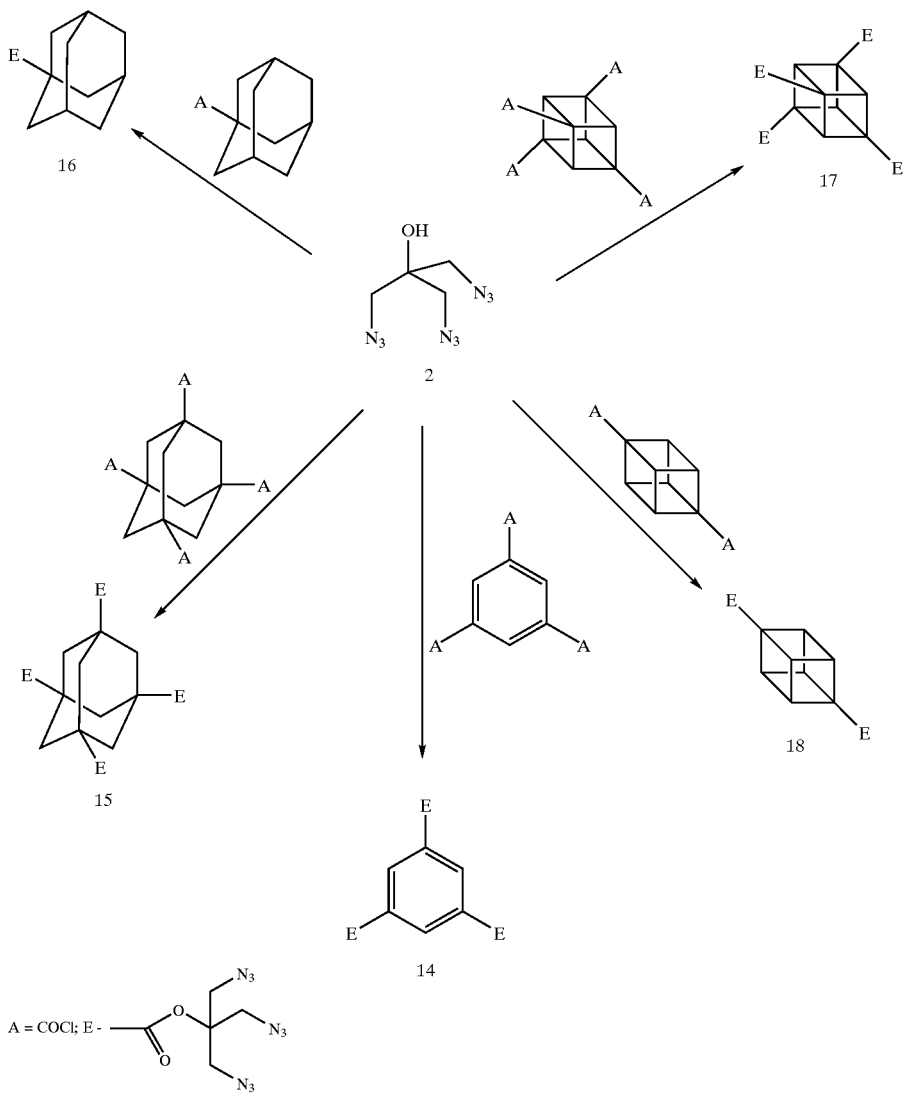

Commercially available benzenitricarbonylchloride was treated with 2-azidomethyl-2-hydroxy-1,3-diazidopropane 2 in refluxing pyridine to obtain the corresponding triester benzene-1,3,5-tricarboxylic acid tris(2-azido-1,1-bisazidomethyl-ethyl)ester 14. The polyesters adamantane 1,3,5,7-tetracarboxylic acid tetrakis(2-azido-1,1-bisazidomethyl-ethyl)ester 15, adamantane carboxylic acid 2-azido-1,1-bisazidomethyl-ethyl)ester 16, cubane 1,3,5,7-tetracarboxylic acid tetrakis (2-azido-1,1-bisazidomethyl-ethyl)ester 17, and cubane 1,4-dicarboxylic acid bis(2-azido-1,1-bisazidomethyl-ethyl)ether 18 were prepared by first converting 2-azidomethyl-2-hydroxy-1,3-diazidopropane 2 to its sodium salt by reaction with sodium hydride and then adding the carbonyl chlorides.

All new compounds prepared and claimed herein were characterized by spectral data and/or x-ray crystallography.

EXPERIMENTAL PROCEDURES

Example 1

Preparation of Methallyldiazide, 6

To a solution of methallyl dichloride (10 g, 0.08 mol) in acetone (200 mL) was added sodium azide (11.4 g, 0.175 mol) and the resulting suspension was heated under reflux for 16 hours. The reaction mixture was then cooled to room temperature and filtered to remove solids (sodium chloride and excess sodium azide), which were washed with one portion of acetone (25 mL). The collected filtrate was concentrated under reduced pressure to obtain methallyl diazide 6. $^1$H NMR (CDCl$_3$): 63.85 (s, 4H), 5.29 (s, 2H).

Example 2

Preparation of 1,3-Diazidoacetone, 7

Methallyldiazide 6(2.5 g) was dissolved in methanol (100 mL) in a round bottom flask and cooled to 78° C. Ozone was bubbled into the solution for 1.5 hrs till blue color persisted. Dimethyl sulfide (2 mL) was added to the reaction mixture at 78° C. and then the mixture was allowed to warm up to room temperature and stirred at room temperature for 30 minutes. The reaction mixture was then concentrated in vacuo to obtain 1,3-diazidoacetone, 7. $^1$H NMR (CDCl$_3$) δ4.07 (s)

Example 3

Preparation DNPH Derivative of 1,3-Diazidoacetone 7

N-2(azido-1-azidomethyl-ethylidene)-N"-(2,4-dinitrophenyl)-hydrazine (7-DNPH):To a suspension of 0.25 g of 2,4-dinitrophenylhydrazine in 5 ml of methanol and was added add 0.5 ml of concentrated sulphuric acid cautiously. The warm solution was filtered and added to a solution of 1,3-diazidoacetone (150 mg) in 2 ml of methanol. Solid N-2(azido-1-azidomethyl-ethylidene)-N"-(2,4-dinitrophenyl)-hydrazine 7-DNPH formed and was collected by filtration and recrystallized from ethanol. $^1$H NMR (CDCl$_3$) δ 9.16 (s, 1H), 8.39 (d, 2H), 7.98 (d, 2H), 4.33 (s, 2H), 4.15 (s, 2H)$^{13}$C NMR (CDCl$_3$) δ145.807, 144.568, 139.227, 130.620, 130.198, 123.197, 116.532, 54.791, 47.764.

Example 4

Preparation of 1,3-Bis(4-carboxytriazolyl)-2,2-dinitropropane 12

Dissolved 2,2-dinitro-1,3-diazidopropane 5 in CDCl$_3$ in an nmr tube. Added a few drops of propiolic acid (excess). Heated the tube at 60° C. for 3 hrs. Decanted out the solution. The residue was dissolved in DMSO. Water was added to the DMSO solution. The product, 1,3-bis(4-carboxytriazolyl)-2,2-dinitropropane 12, was precipitated out and was collected by filtration. $^1$H NMR (DMSO-d$_6$) δ8.70 (s, 2H), 5.98 (s, 4H) $^{13}$C NMR (DMSO-d$_6$) δ162.045, 140.792, 132.454, 116.124, 50.668.

Example 5

Preparation of 2-Oximido-1,3-diazidopropane, 8

To a solution of 1,3-diazidoacetone (2.5 g from the above reaction) in ethanol (150 mL), was added hydroxylamine hydrochloride (1.48 g) and sodium acetate (5.83 g). The reaction mixture was stirred at room temperature for 48 hours. Water was then added and the reaction mixture was extracted with ether. The combined organic layer was washed with water and saturated sodium bicarbonate solution. The organic layer was then dried over sodium sulfate and concentrated under reduced pressure. The resulting residue was chromatographed on silica gel to obtain 2-oximido-1,3-diazidopropane 8. $^1$H NMR (CDCl$_3$) δ4.27 (s, 2H), 3.99 (s, 2H), 8.99 (s, 1H); $^{13}$C NMR (CDCl$_3$) δ151.94, 51.06, 45.31

Example 6

Preparation of 2,2-Dinitro-1,3-diazidopropane, 5

To a refluxing solution of 2-oximido-1,3-diazidopropane (1.2 g) in methylene chloride (30 mL) was added dropwise, a solution of concentrated nitric acid (6 mL) in methylene chloride (10 ml) to which catalytic amounts of urea and ammonium nitrate were added. The reaction mixture was heated under reflux for an additional 2 hrs till the blue green color was gone. The reaction mixture was then cooled to room temperature, diluted with water and the resulting solution was extracted with ethyl acetate. The organic layer was dried over sodium sulfate and concentrated under reduced pressure. The resulting residue was chromatographed to obtain 2,2-dinitro-1,3-diazidopropane 5.$^1$H NMR (CD$_3$COCD$_3$): δ 4.7 (s); $^{13}$C NMR (CD$_3$COCD$_3$): 650.73, 115.14

Example 7

Preparation of Methallyldiazide dimer, (6-DIMER)

Methallyl diazide 6 on standing under ambient conditions for 4–6 weeks deposited crystals which were filtered and washed with hexane and recrystallized from ethanol to obtain 6-DIMER). $^1$H NMR (CDCl 3): δ 3.29 (AB, $J_{AB}$=14.9 Hz, 2H), 4.10, (AB,$J_{AB}$=14.9 Hz, 2H); 3.54 (AB,$J_{AB}$=12.8 Hz, 2H, 3.60 (AB, $J_{AB}$=12.8 Hz, 2H); 4.02 (AB, $J_{AB}$=16.6 Hz, 2H), 4.22 (AB, $J_{AB}$=16.6 Hz, 2H); $^{13}$C NMR (CDCl$_3$): δ 43.99, 50.95, 61.00, 72.83

Example 8

2-Azido-2-azidomethyl-1,3-diazidopropane 1

A suspension of methallyl diazide 6 (0.35 gm, 2.5 mmol), sodium azide (2.5 gm, 38.5 mmol), and manganese (III) acetate in acetic acid (10 mL) was heated at 85° C. for 20 minutes and then at 105° C. for 30 minutes. The resulting pale yellow homogeneous solution was cooled to room temperature and poured into water (100 mL). The mixture was then extracted with methylene chloride (3×25 mL). The organic extracts were combined, dried over sodium sulfate and concentrated, and the residue was purified chromatographically to obtain 2-azido-2-azidomethyl-1,3-diazidopropane 1, as a clear colorless oil. $^1$H NMR (CDCl$_3$): δ3.51 (s); $^{13}$C NMR (CDCl$_3$): 52.91, 64.92.

Example 9

2,2-Bis(azidomethyl)oxirane, 10

A suspension of methallyl diazide (5.5 gm, 0.04 mol) and mcpba (9.5 gm, 77% max) in 1,2-dichlorethane was heated under reflux for 14 hours. The reaction mixture was cooled to room temperature and filtered. The filtrate was washed with saturated sodium bicarbonate solution (2×100 mL). The organic layer was dried over sodium sulfate and concentrated under reduced pressure to provide a residual oil with some solids. The residue was dissolved in ether and the ethereal solution was washed with saturated sodium bicarbonate solution (2×100 mL), dried over sodium sulfate and concentrated under reduced pressure to obtain 2,2-Bis(azidomethyl)oxirane, 10. $^1$H NMR (CDCl$_3$): 62.88 (s, 1H), AB quartet centered at 3.50 (4H, 13.3 Hz), 2.90 (s, 2H).

Example 10

2-Azidomethyl-2-hydroxy-1,3-diazidopropane 2

A. From 2,2-Bis(azidomethyl)oxirane, 10

To a solution of methallyldiazide 6 (0.5 gm, 3.25 mmol) in acetone (20 mL) and water (5 mL) was added sodium azide (0.34 gm, 5.23 mmol) and the resulting mixture was heated under reflux for 3 hours. The reaction mixture was concentrated under reduced pressure and the residue was partitioned between methylene chloride and waster. The organic layer was separated, dried over sodium sulfate and concentrated under reduced pressure. The residue was chromatographed on silica gel to obtain pure 2-azidomethyl-2-hydroxy-1,3-diazidopropane 2. $^1$H NMR (CDCl$_3$): δ2.80 (s, br, 1H), 3.40 (s, 6H); $^{13}$C NMR (CDCl$_3$): δ54.53, 74.40.

B. From 2,2-Bis(chloromethyl)oxirane, 9

To a solution of 1,3-diazidoacetone 7 (10 gms, 0.07 mol) in aq. acetone (20 mL water, 150 mL acetone) was added sodium azide (15 gm, 0.23 mol) and the resulting mixture was heated under reflux for 14 hours. The reaction mixture was concentrated under reduced pressure and partitioned between water and methylene chloride. The organic layer was separated, dried over sodium sulfate and concentrated to obtain a residue that was chromatographed to obtain pure 2-azidomethyl-2-hydroxy-1,3-diazidopropane 2.

Example 11

Tris(4-carboxytriazolomethyl)methanol, 13

To a solution of 2-azidomethyl-2-hydroxy-1,3-diazidopropane 2 (0.19 gm), in chloroform was added propiolic acid (0.22 gms) and the solution was heated at reflux for 14 hours. The precipitated product was filtered, and recrystallized from water to obtain pure tris(4-carboxytriazolomethyl)methanol 13. $^1$H NMR (DMSO-d6): δ4.57 (s, 6H), 6.10 (s, 1H), 8.55 (s, 3H).

Example 12

2-Azidomethyl-2-nitrato-1,3-diazidopropane 3

To a cooled (0° C.) solution of nitronium tetrafluoroborate (130 mg, 1.12 mmol) in acetonitrile (2 mL) under nitrogen atmosphere a solution of collidine (127 mg, 1.04 mmol) in acetonitrile (1 mL) was added drop-wise via syringe. The resulting mixture was stirred at 0° C. for 45 min. 2-Azidomethyl-2-hydroxy-1,3-diazido propane, 2, (100 mg, 0.5 mmol) in acetonitrile (2 mL) was added drop-wise and the resulting mixture was stirred at room temperature for 48 hours. The reaction mixture was poured over water (25 mL) and extracted with ethyl acetate (2×15 mL). The combined organic layer was washed with water (1×25 mL), brine (1×25 mL) and dried (Na$_2$SO$_4$). Evaporation of the solvent and chromatographic purification of the residue afforded the 2-azidomethyl-2-nitrato-1,3-diazidopropane 3 as a colorless liquid. $^1$H NMR (CDCl$_3$): δ3.78 (s, 6H); $^{13}$C NMR (CDCl$_3$): δ0.31, 89.07.

Example 13

2-Azidomethyl-2-nitro-1,3-diazidopropane 4

To a solution of the trimesylate, methanesulfonic acid 3-methanesulfonyloxy-2-methanesulfonyloxymethyl-2-nitro-propyl ester 11 (1 gm, 2.6 mmol) in dimethylformamide (10 mL) was added sodium azide (0.6 gm, 9.2 mmol) and the resulting mixture was heated under reflux for 14 hours. The reaction mixture was then cooled to room temperature, diluted with water (50 mL) and extracted with ethyl acetate (50 mL). The organic extract was washed with water, dried over sodium sulfate and concentrated under reduced pressure to give a residue that was chromatographed to obtain pure 2-azidomethyl-2-nitro-1,3-diazidopropane 4. $^1$H NMR (CD$_3$COCD$_3$): 64.01 (s); $^{13}$C NMR (CD$_3$COCD$_3$): 60.36, 95.30.

Example 14

Reaction of 2-azidomethyl-2-hydroxy-1,3-diazidopropane 2 with benzene tricarbonyl chloride

Benzene-1,3,5-tricarboxylic acid tris(2-azido-1,1-bisazidomethyl-ethyl)ester 14

To a solution of 2-azidomethyl-2-hydroxy-1,3-diazidopropane 2 (0.4 gm) in dry pyridine (10 mL) was added benzene tricarbonyl chloride (0.18 gm) and the resulting mixture was heated at reflux overnight. The mixture was then allowed to cool to room temperature and concentrated under reduced pressure. The residue was triturated with ethyl acetate and filtered. The filtrate was concentrated and the residue was chromatographed on silica gel to obtain pure triester benzene-1,3,5-tricarboxylic acid tris(2-azido-1,1-bisazidomethyl-ethyl)ester 14. $^1$H NMR (CDCl$_3$): 63.91 (s, 6H), 8.8 (s, 1H); $^{13}$C NMR (CDCl$_3$): 51.25, 84.08, 130.98, 135.52, 163.53.

Example 15

Reaction of 2-azidomethyl-2-hydroxy-1,3-diazidopropane 2 with cubane dicarbonyl chloride Cubane 1,4-dicarboxylic acid bis(2-azido-1,1-bisazidomethyl-ethyl)ester 18

To a solution of 2-azidomethyl-2-hydroxy-1,3-diazidopropane 2 (0.5 gm) in a dry THF (25 ml) was added sodium hydride (125 mg) and the resulting mixture was heated at reflux overnight. The reaction mixture was cooled and cubane dicarbonyl chloride (325 mg.) in THF was added at room temperature and the reaction mixture was heated at reflux for another 24 hrs. The mixture was then allowed to cool and THF was removed from under reduced pressure and ethyl acetate solvent was added. The resulting solution was washed with dilute HCl and saturated sodium chloride solution. The resulting ethyl acetate solution was evaporated and the product was purified with column chromatography to obtain cubane 1,4-dicarboxylic acid bis(2-azido-1,1-bisazidomethyl-ethyl)ester 18. $^1$H NMR (CDCl 3): 63.74 (s, 12H), 4.29 (s, 6H);

Example 16

Reaction of 2-azidomethyl-2-hydroxy-1,3-diazidopropane 2 with cubane tetracarbonyl chloride:

Cubane 1,3,5,7-tetracarboxylic acid tetrakis (2-azido-1,1-bisazidomethyl-ethyl)ester 17:

To a solution of 2-azidomethyl-2-hydroxy-1,3-diazidopropane 2 (0.5 gm) in a dry THF (25 ml) was added sodium hydride (125 mg) and the resulting mixture was heated at reflux overnight. The reaction mixture was cooled and cubane tetracarbonyl chloride (220 mg.) in THF was added at room temperature and the reaction mixture was heated at reflux for another 48 hrs. The mixture was then allowed to cool and THF was removed from under reduced pressure and ethyl acetate solvent was added. The resulting solution was washed with dilute HCl and saturated sodium chloride solution. The resulting ethyl acetate solution was evaporated and the product was purified with column chromatography to obtain cubane 1,3,5,7-tetracarboxylic acid tetrakis (2-azido-1,1-bisazidomethyl-ethyl)ester17. $^1$H NMR (CDCl): δ3.75 (s, 24H), 4.79 (s, 4H)

Example 17

Reaction of 2-azidomethyl-2-hydroxy-1,3-diazidopropane 2 with Adamantane Tetracarbonyl Chloride: Adamantane 1,3,5,7-tetracarboxylic acid tetrakis(2-azido-1,1-bisazidomethyl-ethyl)ester 15:

To a solution of 2-azidomethyl-2-hydroxy-1,3-diazidopropane 2 (0.5 gm) in a dry THF (25 ml) was added sodium hydride (125 mg) and the resulting mixture was heated at reflux overnight. The reaction mixture was cooled and adamantane tetracarbonyl chloride (240 mg.) in THF was added at room temperature and the reaction mixture was heated at reflux for another 48 hrs. The mixture was then allowed to cool and THF was removed from under reduced pressure and ethyl acetate solvent was added. The resulting solution was washed with dilute HCl and saturated sodium chloride solution. The resulting ethyl acetate solution was evaporated and the product was purified with column chromatography to obtain adamantane 1,3,5,7-tetracarboxylic acid tetrakis(2-azido-1,1-bisazidomethyl-ethyl)ester15. $^1$H NMR (CDCl$_3$): δ3.8 (s), 2.28 (s)

Example 18

Reaction of 2-azidomethyl-2-hydroxy-1,3-diazidopropane 2 with Adamantane Carbonyl Chloride: Adamantane Carboxylic Acid 2-azido-1,1-bisazidomethyl-ethyl)ester 16:

To a solution of 2-azidomethyl-2hydroxy-1,3-diazidopropane 2 (0.5 gm) in a dry THF (25 ml) was added sodium hydride (125 mg) and the resulting mixture was heated at reflux overnight. The reaction mixture was cooled and adamantane carbonyl chloride (990 mg.) in THF was added at room temperature and the reaction mixture was heated at reflux for another 24 hrs. The mixture was then allowed to cool and THF was removed from under reduced pressure and ethyl acetate solvent was added. The resulting solution was washed with dilute HCl and saturated sodium chloride solution. The resulting ethyl acetate solution was evaporated and the product was purified with column chromatography to obtain adamantane carboxylic acid 2-azido-1,1-bisazidomethyl-ethyl)ester 16.

$^1$H NMR (CDCl3): 63.72 (s), 1.97 (s), 1.9 (s), 2.01 (s)

Other features, advantages, and specific embodiments of this invention will become readily apparent to those exercising ordinary skill in the art after reading the foregoing disclosures. These specific embodiments are within the scope of the claimed subject matter unless otherwise expressly indicated to the contrary. Moreover, while specific embodiments of this invention have been described in considerable detail, variations and modifications of these embodiments can be effected without departing from the spirit and scope of this invention as disclosed and claimed.

What is claimed is:

1. 3a,8a-Bis-azidomethyl-3a,4,8a,9-tetrahydro-3H,8H-bis[1,2,3]triazolo[1,5-a;1",5"-d]pyrazine.

* * * * *